US012667303B2

(12) United States Patent 　　　(10) Patent No.: US 12,667,303 B2
McKinnon et al. 　　　(45) Date of Patent: \*Jun. 30, 2026

(54) TECHNOLOGIES FOR INTRA-OPERATIVE LIGAMENT BALANCING USING MACHINE LEARNING

(71) Applicant: SMITH & NEPHEW, INC., Memphis, TN (US)

(72) Inventors: Brian W. McKinnon, Bartlett, TN (US); Scott Laster, Memphis, TN (US)

(73) Assignee: Smith & Nephew, Inc., Memphis, TN (US)

( \* ) Notice: Subject to any disclaimer, the term of this patent is extended or adjusted under 35 U.S.C. 154(b) by 399 days.

This patent is subject to a terminal disclaimer.

(21) Appl. No.: 18/216,321

(22) Filed: Jun. 29, 2023

(65) Prior Publication Data

US 2023/0337969 A1　　Oct. 26, 2023

Related U.S. Application Data

(63) Continuation of application No. 16/482,128, filed as application No. PCT/US2018/016652 on Feb. 2, 2018, now Pat. No. 11,723,586.

(Continued)

(51) Int. Cl.
　　*A61B 34/30*　　　　(2016.01)
　　*A61B 5/00*　　　　(2006.01)
　　　　(Continued)

(52) U.S. Cl.
　　CPC .......... *A61B 5/4533* (2013.01); *A61B 5/4585* (2013.01); *A61B 5/7267* (2013.01);
　　　　(Continued)

(58) Field of Classification Search
　　CPC ... A61B 5/4533; A61B 5/7267; A61B 5/4585; A61B 2034/105; A61B 2562/0252;
　　　　(Continued)

(56) References Cited

U.S. PATENT DOCUMENTS 9,633,410 B2 * 4/2017 Zhou ......................... G06T 1/60
9,633,627 B2 * 4/2017 Joo ........................... H04N 5/63
(Continued)

OTHER PUBLICATIONS

Xiao et al., A Patient-Specific Model for Predicting Tibia Soft Tissue Insertions From Bony Outlines Using a Spatial Structure Supervised Learning Framework, 2016, IEEE, p. 638-646 (Year: 2016).*
(Continued)

*Primary Examiner* — Mcdieunel Marc
(74) *Attorney, Agent, or Firm* — KDW Firm PLLC

(57) ABSTRACT

A computing system having at least one sensor, at least one processor, and at least one memory including a plurality of instructions stored thereon that, in response to execution by the at least one processor, causes the computing system to receive one or more surgical parameters associated with a ligament balancing of a patient's joint, receive real-time sensor data generated by the at least one sensor and indicative of at least one characteristic of the patient's joint, and apply machine learning to determine a next ligament balancing step of the ligament balancing of the patient's joint based on the one or more surgical parameters and the real-time sensor data, wherein the next ligament balancing step is a step of one or more steps intended to result in a target state of the patient's joint identified by the machine learning.

20 Claims, 6 Drawing Sheets

Related U.S. Application Data

(60) Provisional application No. 62/504,245, filed on May 10, 2017, provisional application No. 62/453,739, filed on Feb. 2, 2017.

(51) Int. Cl.

| | |
|---|---|
| *A61F 2/46* | (2006.01) |
| *A61B 5/11* | (2006.01) |
| *A61B 34/10* | (2016.01) |
| *G06N 3/02* | (2006.01) |
| *G06N 20/00* | (2019.01) |

(52) U.S. Cl.

CPC ............. *A61F 2/468* (2013.01); *A61B 5/1121* (2013.01); *A61B 5/4836* (2013.01); *A61B 34/10* (2016.02); *A61B 2034/105* (2016.02); *A61B 34/30* (2016.02); *A61B 2562/0247* (2013.01); *A61B 2562/0252* (2013.01); *A61B 2562/0261* (2013.01); *A61F 2/4657* (2013.01); *G06N 3/02* (2013.01); *G06N 20/00* (2019.01)

(58) Field of Classification Search

CPC ....... A61B 5/4528; A61B 34/10; A61B 34/30; A61B 2562/0261; A61B 2562/0247; A61B 5/4836; A61B 5/1121; A61F 2/468; A61F 2002/4666; A61F 2/38; A61F 2/4657; G06N 3/02; G06N 20/00

See application file for complete search history.

(56) References Cited

U.S. PATENT DOCUMENTS

| | | | |
|---|---|---|---|
| 10,376,332 B2 | 8/2019 | Colwell, Jr. et al. | |
| 10,766,136 B1 * | 9/2020 | Porter .................... | G06N 3/045 |
| 10,766,137 B1 * | 9/2020 | Porter ..................... | B25J 9/163 |
| 10,792,810 B1 * | 10/2020 | Beckman ................ | B25J 9/163 |
| 10,800,040 B1 * | 10/2020 | Beckman ............... | B25J 9/1605 |
| 10,843,332 B2 | 11/2020 | Walsh et al. | |
| 11,298,246 B1 | 4/2022 | Cole et al. | |
| 11,723,586 B2 * | 8/2023 | McKinnon ............. | A61F 2/468 |
| | | | 600/587 |
| 2003/0153978 A1 | 8/2003 | Whiteside | |
| 2007/0233267 A1 | 10/2007 | Amirouche et al. | |
| 2010/0010506 A1 | 1/2010 | Murphy | |
| 2015/0106024 A1 | 4/2015 | Lightcap et al. | |
| 2016/0175117 A1 | 6/2016 | Colwell, Jr. et al. | |
| 2017/0360512 A1 | 12/2017 | Couture et al. | |
| 2019/0183411 A1 | 6/2019 | Yildirim et al. | |
| 2019/0272917 A1 | 9/2019 | Couture et al. | |
| 2019/0388174 A1 | 12/2019 | Colwell, Jr. et al. | |
| 2020/0405396 A1 | 12/2020 | McGuan et al. | |
| 2021/0391058 A1 | 12/2021 | Kostrzewski et al. | |
| 2022/0031473 A1 | 2/2022 | Carter et al. | |
| 2022/0218431 A1 | 7/2022 | Kostrzewski et al. | |
| 2023/0072295 A1 | 3/2023 | McCandless et al. | |

OTHER PUBLICATIONS

Constantinescu et al., Constrained Statistical Modelling of Knee Flexion From Multi-Pose Magnetic Resonance Imaging, 2016, IEEE, p. 1-10 (Year: 2016).*

Valero-Cuevas et al., Computational Models for Neuromuscular Function, 2009, IEEE, p. 110-135 (Year: 2009).*

Liu et al., Classification of knee joint vibroarthrographic signals using k-nearest neighbor algorithm, 2014, IEEE, p. 1-4 (Year: 2014).*

International Search Report and Written Opinion for International Patent Application No. PCT/US2018/016652, mailed Apr. 12, 2018, 9 pages.

Plate, J. F., et al., "Achieving Accurate Ligament Balancing Using Robotic-Assisted Unicompartmental Knee Arthroplasty", Advances in Orthopedics, vol. 2013, pp. 1-6, Jan. 1, 2013.

Verstraete et al., The application of machine learning to balance a total knee arthroplasty, published Jun. 2020 via Bone Joint Open, pp. 236-233.

* cited by examiner

300

MEDIAL FORCE

LATERAL FORCE

POSITION OF MEDIAL CONTACT POINT

POSITION OF LATERAL CONTACT POINT

ANTHROPOMETRIC CHARACTERISTICS

GENDER

LIGAMENT CONDITION

NEURAL NETWORK

LIGAMENT RELEASE

TECHNOLOGIES FOR INTRA-OPERATIVE LIGAMENT BALANCING USING MACHINE LEARNING

CROSS-REFERENCE TO RELATED APPLICATIONS

This application is a continuation application of U.S. patent application Ser. No. 16/482,128, filed Jul. 30, 2019, which is a United States National Phase filing of International Application No. PCT/US2018/016652, filed Feb. 2, 2018, which claims the benefit of U.S. Provisional Patent Application Ser. No. 62/453,739, filed Feb. 2, 2017, and claims the benefit of U.S. Provisional Patent Application Ser. No. 62/504,245, filed May 10, 2017, the entire contents of each application is hereby incorporated by reference in its entirety.

BACKGROUND

Total knee replacement surgery typically involves ligament balancing and/or the adjustment of bone resections or the placement/position of implants, which thereby adjusts the tension in various ligaments in the patient's knee in order to ensure that the patient's knee is stable throughout a range of motion. Ligament balancing may also be performed, for example, to reduce the patient's pain from tight structures, increase the range of motion of the patient due to ligament tightness, and/or boost rehabilitation and recovery following surgery.

A surgeon may utilize various techniques to adjust ligament tension during ligament balancing procedures. For example, the surgeon may release (i.e., cut) one or more of the ligaments that surround the knee in a controlled manner. Various soft tissue structures including, for example, the posterior oblique ligament, the superficial medial collateral ligament, the pes anserinus tendons, the lateral collateral ligament, the popliteus tendon, the iliotibial band, and/or other ligaments may be released in various locations and/or along various planes.

The surgeon may, alternatively or additionally, adjust ligament tension by substituting different implant options where the thickness of the implant changes the overall or global ligament tension in the knee. An assortment of trial components, particularly for the tibia, is typically available in different thicknesses to facilitate ligament balancing techniques. In other embodiments, ligament tension may be adjusted by adjusting the bony resections to accommodate proper ligament balancing where, for example, one can plan to remove 1 mm more or less tibia bone to loosen or tighten the overall spaces in both extension and flexion holistically. Further, the surgeon may adjust ligament tension by adjusting overall implant positions for accommodation of the proper ligament tensions. For example, in some circumstances, a femoral implant may be selected that is larger than the "ideal" size and shifted posterior into the flexion space to tighten the flexion ligaments.

Achieving a particular ligament balance result often depends significantly on the surgeon's skill, experience, and training. Such training often requires surgeons to rely on tactile discernment or a "feel" to determine whether they have achieved the appropriate ligament balance. If the ligaments are not properly balanced by the surgeon, it may result in a poorly performing and/or unstable knee.

SUMMARY

In one embodiment, a computing system may include at least one sensor, at least one processor, and at least one memory comprising a plurality of instructions stored thereon that, in response to execution by the at least one processor, causes the computing system to receive one or more surgical parameters associated with a ligament balancing of a patient's joint, receive real-time sensor data generated by the at least one sensor and indicative of at least one characteristic of the patient's joint, and apply machine learning to determine a next ligament balancing step of the ligament balancing of the patient's joint based on the one or more surgical parameters and the real-time sensor data, wherein the next ligament balancing step is a step comprising one or more steps intended to result in a target state of the patient's joint identified by machine learning. Further embodiments, forms, features, and aspects of the present application shall become apparent from the description and figures provided herewith.

BRIEF DESCRIPTION OF THE DRAWINGS

The concepts described herein are illustrative by way of example and not by way of limitation in the accompanying figures. For simplicity and clarity of illustration, elements illustrated in the figures are not necessarily drawn to scale. Where considered appropriate, references labels have been repeated among the figures to indicate corresponding or analogous elements.

DETAILED DESCRIPTION

Figure 1:
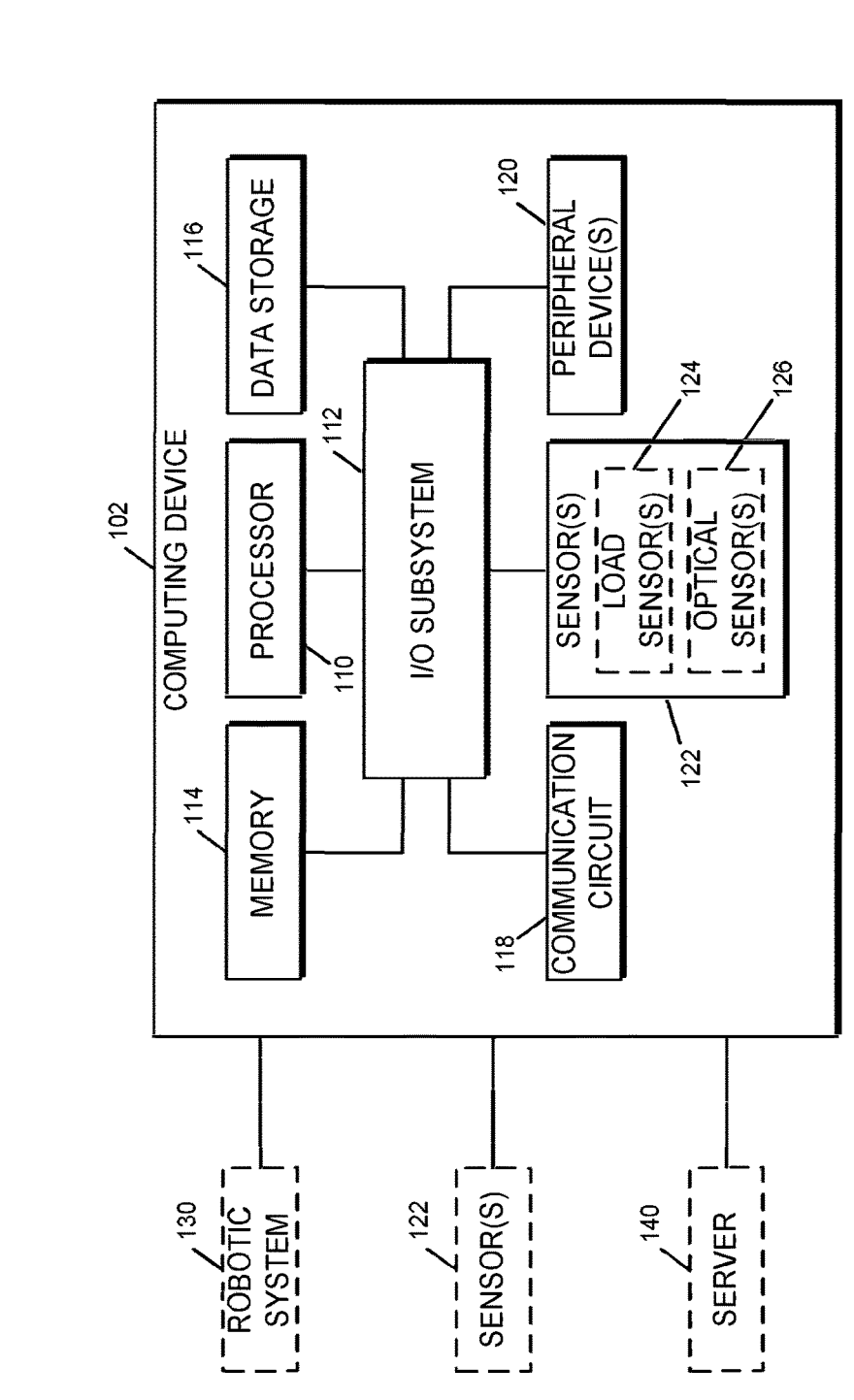
FIG. 1 is a simplified block diagram of a system for intra-operative ligament balancing using machine learning according to one form of the invention.

Although the concepts of the present disclosure are susceptible to various modifications and alternative forms, specific embodiments have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should further be appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described. Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Further, with respect to the claims, the use of words and phrases such as "a," "an," "at least one," and/or "at least one portion" should not be interpreted so as to be limiting to only one such element unless specifically stated to the contrary, and the use of phrases such as "at least a portion" and/or "a portion" should be interpreted as encompassing both embodiments including only a portion of such element and embodiments including the entirety of such element unless specifically stated to the contrary.

The disclosed embodiments may, in some cases, be implemented in hardware, firmware, software, or a combination thereof. The disclosed embodiments may also be implemented as instructions carried by or stored on one or more transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than that shown in the illustrative figures. Additionally, the inclusion of a structural or method feature in a particular figure is not meant to imply that such feature is required in all embodiments and, in some embodiments, may not be included or may be combined with other features.

Referring now to FIG. 1, shown therein is an illustrative system 100 for intra-operative ligament balancing using machine learning (e.g., using an artificial neural network). As described in detail below, the system 100 receives one or more surgical parameters associated with a ligament balancing of a patient's joint and real-time (or near real-time) sensor data generated by at least one sensor. The sensor data may be indicative of at least one characteristic of the patient's joint. The system 100 may further apply machine learning to determine a next ligament balancing step of a ligament balancing procedure based on the surgical parameters and the real-time sensor data. For example, the system 100 may determine the next ligament balancing step in a series of steps intended to result in a target state (e.g., a properly balanced knee joint) identified by the machine learning. It should be appreciated that, in some embodiments, the techniques described herein may also be applied to the balancing of soft tissue structures other than ligaments (e.g., tendons and/or other soft tissue structures). Although the techniques are described herein primarily in reference to the application of a neural network, it should be appreciated that, in other embodiments, the neural network may be replaced with another suitable machine learning algorithm, technique, and/or mechanism. For example, in various embodiments, the system 100 may utilize a regression algorithm, instance-based algorithm, regularization algorithm, decision tree algorithm, Bayesian algorithm, clustering algorithm, association rule learning algorithm, deep learning algorithm, dimensionality reduction algorithm, and/or other suitable machine learning algorithm, technique, and/or mechanism.

The illustrative computing system 100 includes a computing device 102, which may be embodied as any type of computing device capable of performing the functions described herein. For example, the computing device 102 may be embodied as a desktop computer, laptop computer, tablet computer, notebook, netbook, Ultrabook™ cellular phone, smartphone, wearable computing device, personal digital assistant, mobile Internet device, Internet of Things (IoT) device, server, router, switch, and/or any other computing/communication device capable of performing the functions described herein. As shown in FIG. 1, the illustrative computing device 102 includes a processor 110, an input/output ("I/O") subsystem 112, a memory 114, a data storage 116, a communication circuitry 118, one or more peripheral devices 120, and one or more sensors 122. In other embodiments, the computing device 102 may include other or additional components, such as those commonly found in a typical computing device (e.g., various input/output devices and/or other components). Additionally, in some embodiments, one or more of the illustrative components may be incorporated in the processor 110. Although a single computing device 102 is illustratively shown, it should be appreciated that one or more of the components of the computing device 102 described herein may be distributed across multiple computing devices. In other words, the techniques described herein may be employed by a computing system that includes one or more computing devices.

The processor 110 may be embodied as any type of processor capable of performing the functions described herein. For example, the processor 110 may be embodied as a single or multi-core processor(s), digital signal processor, microcontroller, or other processor or processing/controlling circuit. Similarly, the memory 114 may be embodied as any type of volatile or non-volatile memory or data storage capable of performing the functions described herein. In operation, the memory 114 may store various data and software used during operation of the computing device 102 such as operating systems, applications, programs, libraries, and drivers. The memory 114 is communicatively coupled to the processor 110 via the I/O subsystem 112, which may be embodied as circuitry and/or components to facilitate input/output operations with the processor 110, the memory 114, and other components of the computing device 102. For example, the I/O subsystem 112 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 112 may form a portion of a system-on-a-chip (SoC) and be incorporated, along with the processor 110, the memory 114, and other components of the computing device 102, on a single integrated circuit chip.

The data storage 116 may be embodied as any type of device or devices configured for short-term or long-term storage of data such as, for example, memory devices and circuits, memory cards, hard disk drives, solid-state drives, or other data storage devices. The data storage 116 and/or the memory 114 may store various data during operation of the computing device 102 useful for performing the functions described herein.

The communication circuitry 118 may be embodied as any communication circuit, device, or collection thereof, capable of enabling communications between the computing device 100 and other remote devices (e.g., the server 106) over a network (e.g., the network 104). The communication circuitry 118 may be configured to use any one or more communication technologies (e.g., wireless or wired communications) and associated protocols (e.g., Ethernet, Bluetooth®, Wi-Fi®, WiMAX, etc.) to effect such communication.

The peripheral devices 120 may include any number of additional peripheral or interface devices, such as speakers, microphones, additional storage devices, and so forth. The particular devices included in the peripheral devices 120 may depend on, for example, the type and/or intended use of the computing device 102. For example, in some embodiments, the peripheral devices 120 may include a keyboard, mouse, display, touchscreen display, printer, alarm, status indicator, handheld device, diagnostic tool, reader device, and/or one or more other suitable peripheral devices.

The sensors 122 may be embodied as any sensors configured to sense physical characteristics or features of the patient's joint associated with the ligament balance of the joint. For example, in some embodiments, the sensors 122 may include one or more load/pressure sensors 124 and/or one or more optical sensors 126. The load sensors 124 may generate real-time sensor data indicative of a force applied to the load sensor 124 by the patient's bone (e.g., the femur). For example, in some embodiments, the patient's femur may be moved through a range of motion between flexion and extension of the knee such that the force at various points along the range motion may be measured. Similarly, in some embodiments, the computing system 100 may utilize optical sensors 126 to generate real-time sensor data indicative of a displacement between bones of the patient's joint (e.g., in conjunction with a robotic system 130).

In some embodiments, additional and/or alternative sensors other than those described above may be included in the computing device 102. For example, in various embodiments, the sensors 122 may be embodied as, or otherwise include, light sensors, weight sensors, proximity sensors, electromagnetic sensors, hall effect sensors, audio sensors, temperature sensors, motion sensors, piezoelectric sensors, and/or other types of sensors. Of course, the computing device 102 may also include components and/or devices configured to facilitate the use of the sensors 122. As shown in FIG. 1, it should be appreciated that, in some embodiments, one or more of the sensors 122 may be external or separate from the computing device 102. For example, in some embodiments, one or more of the sensors 122 may form a portion of a robotic system 130 of the system 100 configured for assisting with ligament (or other soft tissue structure) balancing.

As shown in FIG. 1, in some embodiments, the computing system 100 may include a server 140 communicatively coupled to the computing device 102. For example, in some embodiments, the server 140 may include the neural network (or other machine learning data structures), surgical parameters, input/output data of the machine learning algorithm, machine learning training data (e.g., for a neural network), and/or other suitable data for performing the functions described herein. The server 140 may be embodied as any type of computing device capable of performing the functions described herein. For example, the server 140 may be embodied as a server, desktop computer, laptop computer, tablet computer, notebook, netbook, Ultrabook™, cellular phone, smartphone, wearable computing device, personal digital assistant, mobile Internet device, Internet of Things (IoT) device, router, switch, and/or any other computing/communication device capable of performing the functions described herein. In some embodiments, the server 140 may be similar to the computing device 102 described above. For example, the server 140 may include components similar to the components of the computing device 102 described above and, therefore, the descriptions of such components have not been repeated herein for clarity of the description.

Although only one computing device 102 and one server 140 are shown in the illustrative embodiment of FIG. 1, the system 100 may include multiple computing devices 102 and/or servers 140 in other embodiments. For example, in some embodiments, the computing device 102 may communicate with multiple servers 140. Further, in some embodiments, it should be appreciated that the server 140 may be omitted from the computing system 100.

It should be appreciated that the techniques described herein may help surgeons obtain a more consistent and/or improved ligament balancing result relative to current techniques, which often rely on the "feel" of the surgeon. The techniques may have more repeatable results, allow less experienced surgeons to leverage a robust knowledgebase, involve less operating room time, and/or provide the patient with reduced post-operative pain, faster rehabilitation, and/or a more stable joint.

The system 100 may provide guidance to the surgeon regarding the next step(s) to take in order to properly balance the ligaments of the patient's joint. In particular, as described in detail below, the system 100 utilizes machine learning (e.g., using a neural network), which is trained to learn, for example, different patterns or signatures associated with ligament balance. For example, a neural network (or other machine learning algorithm) may be trained to recognize different patterns and understand the effect various ligament releases would have on the ligament balance and/or other features of the patient's joint. In other words, the "know how" incorporated into the neural network may be leveraged by the system 100 to inform the surgeon regarding the current ligament balancing status of a surgery and the appropriate steps (e.g., ligament releases) to perform in order to arrive at the proper ligament balance. As described below, the neural network (or other machine learning algorithm) may accept multiple inputs and may output, for example, the proper treatment with respect to all of the moving parts, whereas the mental model and "feel" frequently used by surgeons places significant limitations on the surgeon's ability to perform the proper treatment in the safest, most effective, and/or most efficient manner.

Figure 2:
FIG. 2 is a simplified diagram of at least one embodiment of a neural network for intra-operative ligament balancing.
Figure 2:
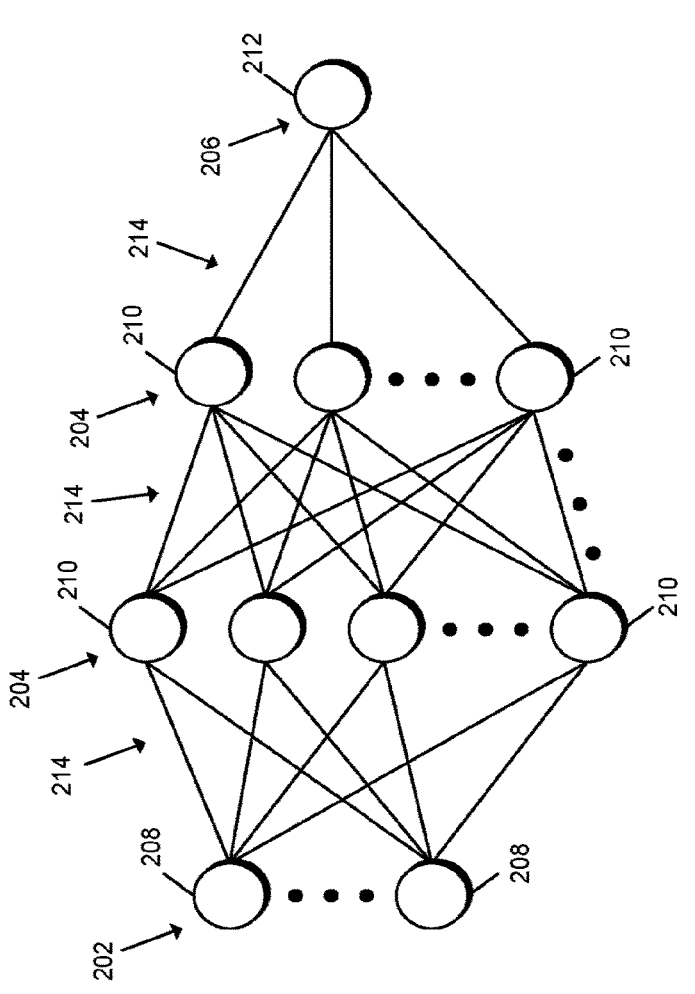

Referring now to FIG. 2, shown therein is an illustrative neural network 200 for intra-operative ligament balancing. It should be appreciated that the neural network 200 is a multi-layered network of nodes that permits self-learning and training based on data associated with ligament balancing. Depending on the particular embodiment, the neural network 200 may be implemented in hardware, firmware, and/or software. For example, in some embodiments, the data associated with the neural network 200 may be stored in a database in the data storage 116 and/or the memory 114 of the computing device 102. In some embodiments, each of the nodes may correspond with one or more designated memory locations. Further, in some embodiments, the neural network 200 may be established in hardware such as, for example, on a controller or control system for efficient processing. As indicated above, it should be appreciated that, in some embodiments, the techniques described herein may also be applied to intra-operative balancing of soft tissue structures other than ligaments. Additionally, in some embodiments, the techniques described herein may apply other machine learning algorithms, techniques, and/or mechanisms in addition to, or alternative to, the neural network 200.

The illustrative neural network 200 includes an input layer 202, one or more hidden layers 204, and an output layer 206. Further, each of the layers 202, 204, 206 includes one or more nodes. In particular, the input layer 202 includes one or more input nodes 208, with each of the hidden layers 204 including one or more hidden nodes 210, and the output layer 206 including one or more output nodes 212. Although the neural network 200 may show a particular number of nodes in a given layer, it should be appreciated that the number of nodes in a given layer may vary depending on the particular embodiment. Further, the number of nodes may vary between layers. Even if the neural network 200 includes multiple hidden layers 210, it should be appreciated that the number of nodes in each of those hidden layers 210 may differ from one another. Each of the nodes of a particular layer is connected to each other node of the adjacent layer with a weighted connection 214 analogous to the synapses of the human brain. In particular, each input node 208 includes a connection 214 to each hidden node 210 of the first hidden layer 204, and those nodes 210 of the first hidden layer 204 are connected to the hidden nodes 210 of the next hidden layer 204, if any. The nodes 210 of the last (or only) hidden layer 204 are connected to the output nodes 212 of the output layer 206. As such, the number of connections may vary widely with the number of nodes in the neural network 200. Further, in some embodiments, one or more connections may be omitted or have a weight of zero.

It should be appreciated that the input nodes 208 correspond with inputs (e.g., input parameters) of the neural network 200, and the output nodes 212 correspond with outputs of the neural network 200. As described in detail below, the input parameters of the neural network 200 may include static parameters (e.g., anthropometric data, etc.) and/or dynamic parameters (e.g., force/load data, gap/displacement data, and/or other sensor data) depending on the particular embodiment. In some embodiments, the outputs include one or more ligament balancing steps for the patient's joint to arrive at a target balanced state. The hidden nodes 210 may facilitate the learning, classification, and/or other functions of the neural network 200. It should be appreciated that the neural network 200 may include an activation function that is configured to convert each neuron's weighted input to its output activation value. In some embodiments, the neural network 200 may utilize a composition of functions such as a nonlinear weighted sum in conjunction with a hyperbolic tangent function, sigmoid function, and/or another suitable activation function. In some embodiments, it should be appreciated that the neural network 200 may store data (e.g., in a database) in the computing device 102 or remotely on the server 140, the robotic system 130, a cloud-based system, and/or in another suitable location.

Figure 3:
FIG. 3 is a simplified diagram of at least one other embodiment of a neural network for intra-operative ligament balancing.
Figure 3:
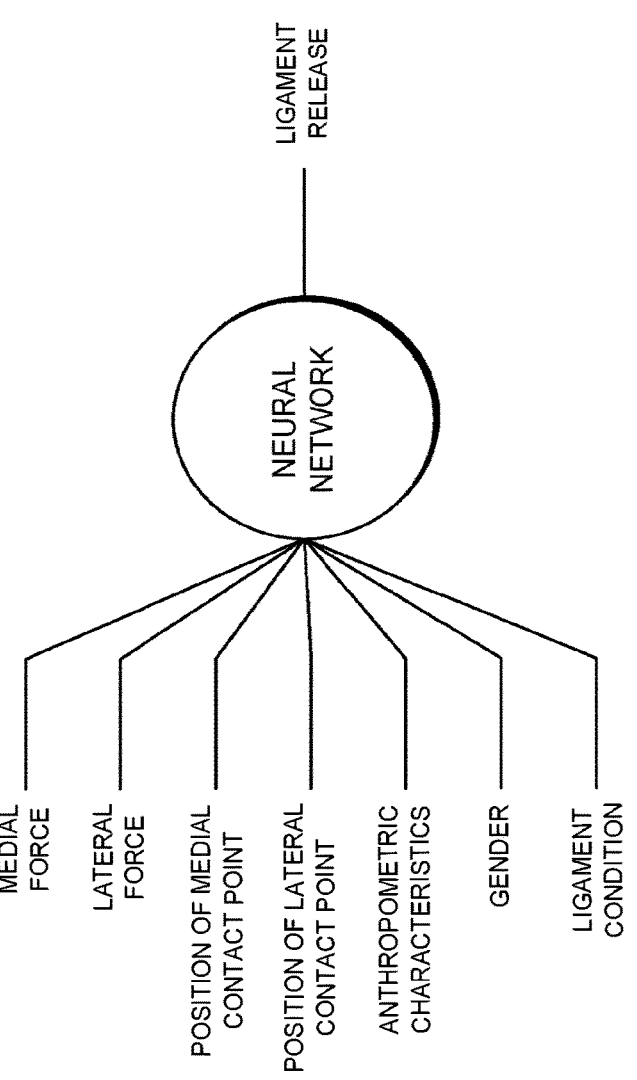

Referring now to FIG. 3, shown therein is another illustrative neural network 300 for intra-operative ligament balancing. It should be appreciated that the neural network 300 may be configured similar to the generalized neural network 200. However, the various internal nodes and connections of the neural network 300 are omitted for clarity. As shown, the illustrative neural network 300 includes seven input parameters and one output parameter. It should be appreciated that the input parameters include both static surgical parameters and dynamic parameters (e.g., sensor data and/or data derived therefrom). In particular, the input parameters include a medial force, lateral force, position of the medial contact point, position of the lateral contact point, anthropometric characteristics of the patient (e.g., height, weight, dimensions, body fat composition, etc.), gender of the patient, and ligament condition of the patient. The output of the neural network 300 identifies a ligament release (e.g., in millimeters) to perform as the next step in the ligament balancing procedure. Armed with the data regarding the amount of release to perform, it should be appreciated that a skilled surgeon would be able to make the proper cuts to the ligament to result in that release.

In some embodiments, the medial and lateral forces are indicative of forces applied to the load sensor(s) 124 at medial and lateral positions of the patient's joint. Similarly, the positions (e.g., relative 'x' and 'y' coordinates) of the medial and lateral contact points are indicative, for example, of the contact points of the medial and lateral condyles of the patient's femur on the load sensor(s) 124 and/or a tibial tray. The ligament condition of the patient may provide a classification of the condition of the ligament tissue of the patient (e.g., via a ranking system, raw measurements, etc.). In other embodiments, it should be appreciated that the neural network 300 may utilize different static and/or dynamic parameters and/or have different output parameters. For example, in some embodiments, the input parameters may include sensor data generated by optical sensors 126 that identifies the gap/displacement of the knee throughout a range of motion. Further, in some embodiments, the static parameters may include the age of the patient, collagen levels of the patient, deterioration level of the patient's bone or ligaments, and/or other suitable parameters. In other embodiments, the particular implants to be used in the surgical procedure may also be provided as static parameters.

Figure 4:
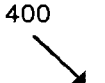
FIG. 4 is a simplified block diagram of at least one embodiment of a method for intra-operative ligament balancing using machine learning.
Figure 4:
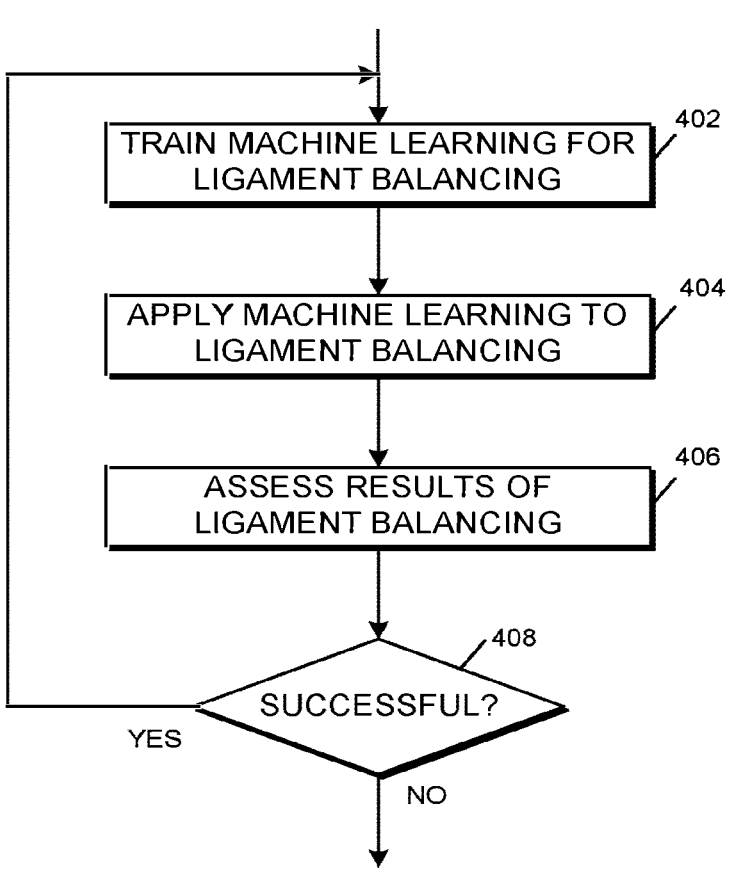

Referring now to FIG. 4, in use, the computing device 102 may execute a method 400 for intra-operative ligament balancing using machine learning. The illustrative method 400 begins with block 402 in which the computing device 102 trains the machine learning algorithm (e.g., a neural network) for ligament balancing. Although the computing device 102 is described herein as training the machine learning algorithm, it should be appreciated that the server 140 and/or one or more computing devices may be used, either separately or in conjunction with the computing device 102, to train the machine learning algorithm.

It should be appreciated that the computing system 100 may utilize a substantial amount of data associated with ligament balancing procedures in order to train the machine learning algorithm. In particular, the computing system 100 may utilize data from computer simulations of ligament balancing procedures, real-world surgeries performed by surgeons, surgeries performed or assisted by the robotic system 130, and/or cadaver-based ligament balancing procedures that result in a proper balance. The machine learning algorithm may be trained based on cases that resulted in good outcomes, and the bad outcomes may be ignored insofar as training the machine learning algorithm is concerned. In ascertaining whether a particular ligament balancing procedure was successful, various techniques may be employed including objective and subjective measures. For example, patients and/or surgeons may prepare questionnaires that indicate their thoughts regarding the success of the procedure, force plates and foot mechanics of the patient may be measured at a gait lab, and electromyography data, muscle-firing patterns, joint stability, and balance may be analyzed, among other characteristics.

It should be appreciated that the machine learning algorithm may be trained for various use cases depending on the particular implementation. For example, in some embodiments, the machine learning algorithm is trained to learn what a particular surgeon does as the operations occur such that the machine learning algorithm is trained based on the surgical preferences of the surgeon. The computing device 102 may record pressures across a range of motion and determine the gaps that the surgeon prefers or finds acceptable. As such, the range of acceptability of a surgeon may be tracked and, once learned, the machine learning algorithm may establish that range as its standard for steering the surgeon (or other surgeons) in the most efficient and effective manner for subsequent procedures involving the application of the machine learning algorithm. In other embodiments, a network of trusted surgeons and/or opinion leaders may be established and the machine learning algorithm may be trained based on their preferences such that another surgeon (e.g., a less experienced surgeon) may rely on the machine learning algorithm taught by those respected surgeons to derive a plan for surgeon's ligament balancing procedure. In some embodiments, the machine learning algorithm learns the most efficient and/or effective step to perform in a ligament balancing procedure at every step throughout the procedure, thereby eliminating guesswork by the surgeon and a reliance on "feel."

As described above, in some embodiments, the machine learning algorithm (e.g., the neural network) may be trained using force data such as, for example, the medial and lateral forces applied to the load sensor(s) 124 at various points through the range of motion of the patient's joint and the position of the medial and lateral contact points through the range of motion in conjunction with various static data associated with the patient (e.g., anthropometric data, gender, age, ligament condition, deterioration levels, etc.). In other embodiments, the computing device 102 may train the machine learning algorithm based on gaps/displacements instead of, or in addition to, pressure measurements. For example, the computing device 102 may track the distal femoral cut and/or other resections and the effect on the gap spacing. Further, the patient's leg may be moved through a range of motion and the optical sensor(s) 126 may measure the displacements/gaps that the knee opens or closes throughout the range of motion, which may be indicative of the looseness/tightness of ligament structures. It should be appreciated that the machine learning algorithm may learn the appropriate steps to arrive at a target ligament balance state for patients having a wide array of characteristics.

In some embodiments, the machine learning algorithm may be trained for each ligament individually. For example, the machine learning algorithm may have the same input parameters described herein with an output parameter corresponding with, for example, the particular ligament release required for that particular ligament (e.g., in millimeters). As such, the machine learning algorithm may inform the surgeon of different approaches to the ligament balancing and/or the benefit of various ligament releases.

In block 404, the computing device 102 applies machine learning to ligament balancing. In other words, the computing device 102 may use the trained machine learning algorithm (e.g., a trained neural network) to assist the surgeon in a ligament balancing procedure by identifying the appropriate steps for the surgeon to perform based on the static and/or dynamic input parameters. In some embodiments, the computing device 102 may execute the method 500 of FIG. 5 described below to apply the machine learning algorithm. In block 406, the computing device 102 assesses the results of the ligament balancing. As described above, subjective and/or objective data may be utilized to determine whether the ligament balancing procedure was successful. If the computing device 102 determines in block 408 that the ligament balancing procedure was successful, the method 400 returns to block 402 in which the machine learning (e.g., the neural network) is updated with the additional data and/or a database is updated. However, the ligament balancing procedure was unsuccessful, the method 400 may terminate.

Figure 5:
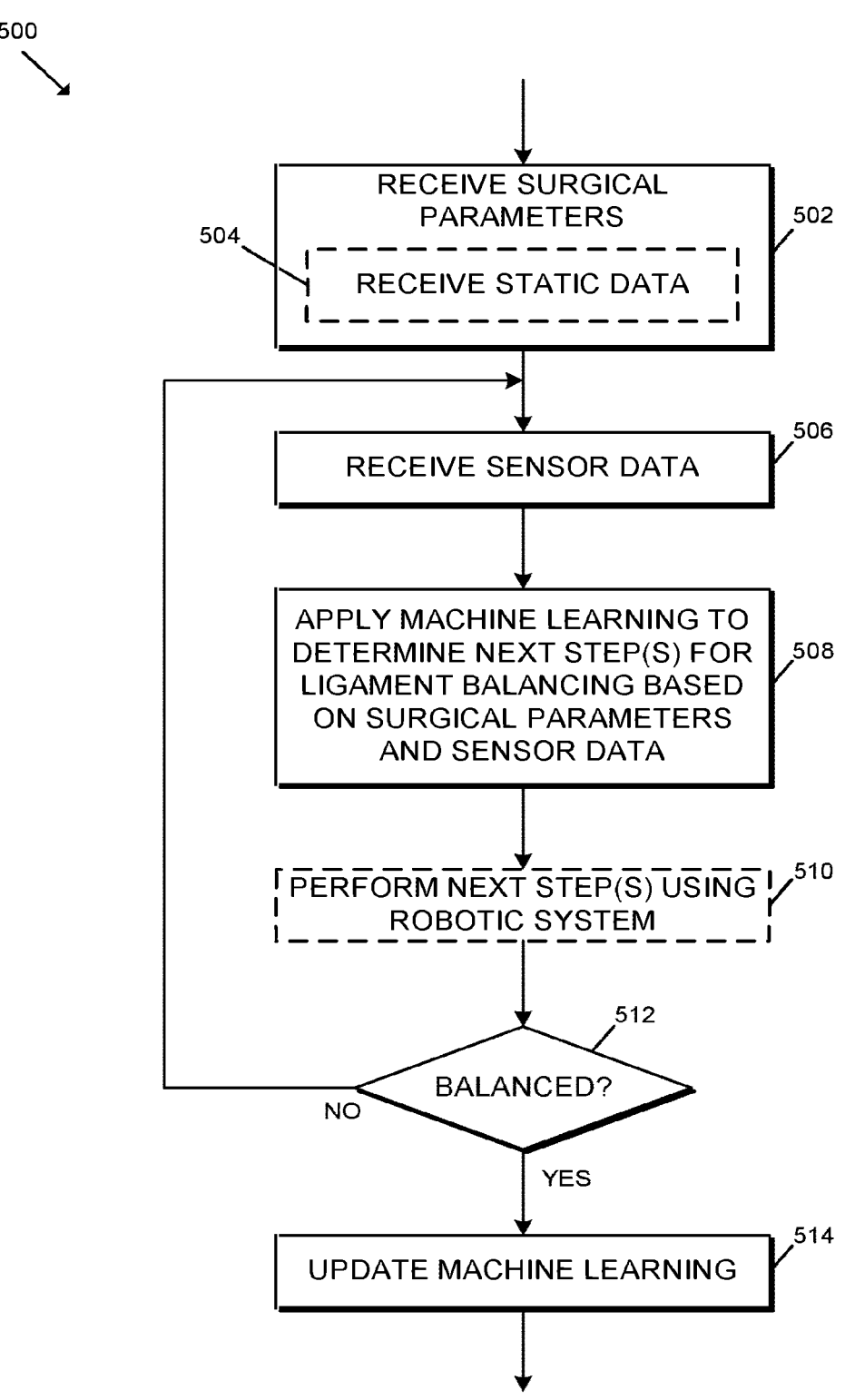
FIG. 5 is a simplified block diagram of at least one embodiment of a method for intra-operative ligament balancing using machine learning.

Referring now to FIG. 5, in use, the computing device 102 may execute a method 500 for intra-operative ligament balancing using machine learning. The illustrative method 500 begins with block 502 in which the computing device 102 receives one or more surgical parameters. In particular, in block 504, the computing device 102 may receive static data. As described above, the surgical parameters may include, for example, anthropometric data of the patient (e.g., height, weight, dimensions, body fat composition, etc.), gender of the patient, age of the patient, ethnicity of the patient, muscularity of the patient, ligament condition of the patient, deterioration levels of various joint structures (e.g., bone, ligaments, etc.) of the patient, collagen levels of the patient, ligament elasticity, prior injuries, patient activities (e.g., sports played), and/or other suitable surgical parameters. In some embodiments, the surgical parameters may also include the particular type of implants to be used on the patient in the surgical procedure. In block 506, the computing device 102 receives sensor data from the sensors 122. In particular, in the illustrative embodiment, the computing device 102 receives the sensor data intra-operatively (e.g., in real-time). As indicated above, the sensor data may include force data, displacement/gap data, and/or other data suitable for performing the ligament balancing procedure.

In block 508, the computing device 102 applies a machine learning algorithm (e.g., a neural network) based on the input parameters (i.e., the surgical parameters and the sensor data) to determine, for example, the next ligament balancing step(s) in the ligament balancing procedure. Depending on the particular embodiment, the output of the machine learning algorithm may be the next ligament balancing step or a sequence (e.g., the entire sequence) of ligament balancing steps to perform to result in the target balanced state of the patient's joint. As indicative above, in some embodiments, the machine learning algorithm identifies the particular ligament release(s) to perform next. In some embodiments, in block 510, the robotic system 130 may be used to perform a ligament balancing step or assist in the performance of that step.

In block 512, the computing device 102 determines whether the ligaments in the patient's joint are properly balanced (e.g., based on the machine learning algorithm). If so, the computing device 102 may further train and/or update the machine learning or database in block 514. However, if the computing device 102 determines that the joint is not properly balanced, the method 500 returns to block 506 in which the computing device 102 again receives sensor data from the sensors 122. In other words, the method 500 may involve a convergent solution to ligament balancing such that the surgeon relies on the machine learning algorithm to determine which ligament balancing step to perform, performs that step, and reassesses using the machine learning algorithm to determine whether further steps are needed.

Accordingly, it should be appreciated that, in embodiments in which the machine learning algorithm identifies a sequence of ligament balancing steps to perform, the surgeon may perform one of those ligament balancing steps and reassess to determine whether the remaining steps in the sequence have changed. It should be further appreciated that the ligament balance that constitutes a properly balanced state may vary depending on the machine learning algorithm and/or the particular implementation. For example, in some embodiments, the machine learning algorithm may direct the surgeon toward an equal medial-lateral balance, whereas in other embodiments, the lateral side may be more lax than the medial side (or vice-versa). Such determinations may be dependent, for example, on the particular implants involved (e.g., symmetric vs. natural knee implants) and/or other relevant parameters.

It should be appreciated that, in some embodiments, the methods 400, 500 described above may involve intra-operative balancing of soft tissue structures other than ligaments, and the methods 400, 500 may apply any suitable machine learning algorithm(s), technique(s), and/or mechanism(s). For example, in some embodiments, the methods 400, 500 may utilize a neural network.

Further, in some embodiments, the techniques described herein may be applied to a bony recut in addition to, or alternative to, a ligament or other soft tissue structure release. For example, in some embodiments, a neural network (or other machine learning algorithm) may be trained for bony cuts and subsequently applied by the computing device 102. It should be appreciated that, in some embodiments, bony cuts may be preferable to ligament releases in order to reduce or eliminate trauma to the patient and/or to improve patient recovery times. In operation, the surgeon may, for example, make a conservative resection of the patient's tibia and utilize the sensor(s) 122 (e.g., load sensors 124 and/or optical sensors 126) in a manner similar to that described above in reference to the ligament release method(s). More specifically, the computing device 102 may leverage the machine learning algorithm to instruct the surgeon regarding any modifications to the conservatively resected tibia, for example, to arrive at the target balance state of the patient's joint. In some embodiments, the surgeon may be able to avoid making any ligament cuts by doing so.

It should be appreciated that the neural network (or other machine learning) associated with bony cuts may utilize inputs and outputs similar to those described in reference to the neural networks 200, 300. Further, the machine learning algorithm may include, for example, one or more inputs associated with the particular implant (e.g., size, shape, model, etc.) and/or one or more outputs associated with the appropriate bone cutting position, alignment, and/or orientation depending on the particular embodiment. In some embodiments, it should be appreciated that one or more neural networks (or other machine learning techniques) may be utilized to recommend both bony cuts and ligament releases appropriate to arrive at the target joint balance.

Figure 6:
FIG. 6 is a simplified diagram of a percentage of force or displacement from neutral of medial and lateral contact points of a patient's knee joint over various degrees of flexion.
Figure 6:
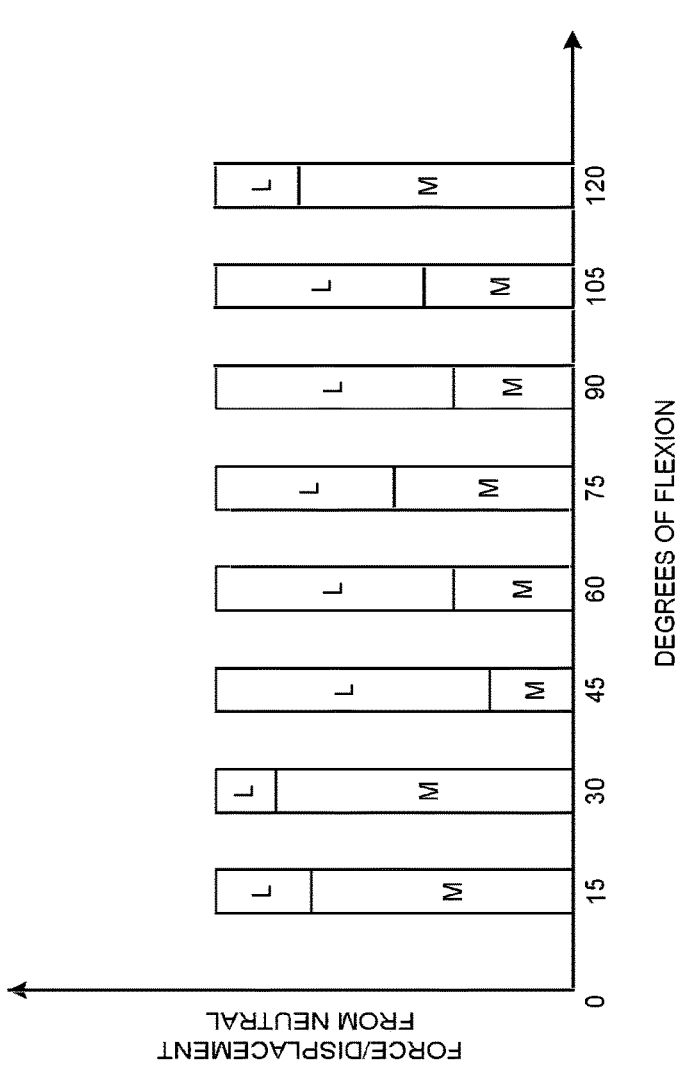

Referring now to FIG. 6, the medial-lateral balance of a patient's knee joint from a neutral position as measured by force and/or displacement data is shown graphically. In particular, the horizontal axis of the graph 600 depicts the range of motion of the knee joint in degrees of flexion. The vertical axis of the graph 600 depicts the force/displacement of the knee joint from neutral in the medial-lateral direction. It should be appreciated that the force/displacement measurements depicted on the vertical axis are normalized values. In some embodiments, such sensed data may be provided to the neural network as input data as described above.

Consistent with the techniques described above, in some embodiments, a robotic-assisted system (e.g., the robotic system 130) where bone trackers are attached to the patient's bone and a tracking system (e.g., optical sensors 126) may be used to measure the position of key points and axes of the femur and tibia in space. In such embodiments, the surgeon may use the tracking system prior to performing cuts and/or take measurements when the procedure is completed.

In one form, a computing system includes at least one sensor, at least one processor, and at least one memory comprising a plurality of instructions stored thereon that, in response to execution by the at least one processor, causes the computing system to receive one or more surgical parameters associated with a ligament balancing of a patient's joint, receive real-time sensor data generated by the at least one sensor and indicative of at least one characteristic of the patient's joint, and apply machine learning to determine a next ligament balancing step of the ligament balancing of the patient's joint based on the one or more surgical parameters and the real-time sensor data, wherein the next ligament balancing step is a step of one or more steps intended to result in a target state of the patient's joint identified by the machine learning.

In some embodiments, the at least one sensor includes a load sensor, and the real-time sensor data is indicative of a force applied to the load sensor by a bone of the patient's joint.

In some embodiments, the real-time sensor data is indicative of a plurality of forces applied to the load sensor by the patient's femur at a plurality of points between flexion and extension of the patient's knee.

In some embodiments, the at least one sensor includes an optical sensor, and the real-time sensor data is indicative of a displacement between bones of the patient's joint.

In some embodiments, the one or more surgical parameters include at least one of a gender of the patient, anthropometric data of the patient, a classification of a condition of a ligament of the patient, or an age of the patient.

In some embodiments, the computing system further includes a robotic system configured to perform the next ligament balancing step.

In some embodiments, applying machine learning includes applying a neural network, and the plurality of instructions further causes the computing system to further train the neural network based on a successful outcome of the ligament balancing of the patient's joint.

In some embodiments, applying machine learning includes applying a neural network, and the neural network includes a plurality of inputs and at least one output, the plurality of inputs includes the one or more surgical parameters and the real-time sensor data, and the at least one output includes the next ligament balancing step.

In some embodiments, the at least one output includes an ordered sequence of ligament balancing steps to result in the target state of the patient's joint.

In some embodiments, the next ligament balancing step identifies an amount of release of a specific ligament of the patient's joint.

In another form, a method for intra-operative ligament balancing using a neural network includes receiving, by a computing system, one or more surgical parameters associated with a ligament balancing of a patient's joint, receiving, by the computing system, real-time sensor data generated by at least one sensor and indicative of at least one characteristic of the patient's joint, and applying, by the computing system, a neural network to determine a next ligament balancing step of the ligament balancing of the patient's joint based on the one or more surgical parameters and the real-time sensor data, wherein the next ligament balancing step is a step of one or more steps intended to result in a target state of the patient's joint identified by the neural network.

In some embodiments, the one or more surgical parameters includes at least one of a gender of the patient, anthropometric data of the patient, a classification of a condition of a ligament of the patient, or an age of the patient.

In some embodiments, the neural network includes a plurality of inputs and at least one output, the plurality of inputs includes the one or more surgical parameters and the real-time sensor data, and the at least one output includes the next ligament balancing step.

In some embodiments, the at least one output includes an ordered sequence of ligament balancing steps to result in the target state of the patient's joint.

In some embodiments, the next ligament balancing step identifies an amount of release of a specific ligament of the patient's joint.

In another form, one or more machine-readable storage media comprising a plurality of instructions stored thereon that, in response to execution by a computing device, may cause the computing device to receive one or more surgical parameters associated with a ligament balancing of a patient's joint, receive real-time sensor data generated by at least one sensor and indicative of at least one characteristic of the patient's joint, and apply a neural network to determine a next ligament balancing step of the ligament balancing of the patient's joint based on the one or more surgical parameters and the real-time sensor data, wherein the next ligament balancing step is a step of one or more steps intended to result in a target state of the patient's joint identified by the neural network.

In some embodiments, the at least one sensor includes a load sensor, and the real-time sensor data is indicative of a force applied to the load sensor by a bone of the patient's joint.

In some embodiments, the at least one sensor includes an optical sensor, and the real-time sensor data is indicative of a displacement between bones of the patient's joint.

In some embodiments, the neural network includes a plurality of inputs and at least one output, the plurality of inputs includes the one or more surgical parameters and the real-time sensor data, and the at least one output includes the next ligament balancing step. In some embodiments, the one or more surgical parameters includes at least one of a gender of the patient, anthropometric data of the patient, a classification of a condition of a ligament of the patient, or an age of the patient.

We claim:

1. A method for training a machine learning algorithm to predict one or more ligament balancing steps in a joint replacement procedure, comprising:

receiving, by a processor, a plurality of input data values comprising one or more surgical parameters associated with the one or more ligament balancing of the joint and one or more real-time sensor data indicative of at least one characteristic of the joint, wherein the plurality of inputs data values are inputted into the machine learning algorithm executing on the processor;

computing, by the processor, using the machine learning algorithm, a pattern indicated by the one or more surgical parameters and the one or more real-time sensor data, wherein the machine learning algorithm is trained on a plurality of input data values from previous joint replacement procedures;

computing, by the machine learning algorithm executing on the processor, a next ligament balancing step based on the pattern, wherein data corresponding to the next ligament balancing step is outputted by the processor;

iteratively repeating computation of a subsequent ligament balancing step, based on the one or more real-time sensor data and the one or more surgical parameters, inputted into the processor, wherein one or more ligament balancing results, for each computation, are outputted by the processor;

assessing, by the processor, a success of the ligament balancing, for each of the one or more ligament balancing results, relative to a target ligament balance state identified by the machine learning algorithm; and performing, by the processor, an iteration of training of the machine learning algorithm with one or more input data values associated with the target ligament balance state.

2. The method of claim 1, wherein the one or more surgical parameters comprise one or more demographic data of the patient, muscularity of the patient, ligament condition of the patient, deterioration levels of various joint structures of the patient, collagen levels of the patient, ligament elasticity of the patient, prior injuries of the patient and patient activities.

3. The method of claim 1, wherein the joint replacement procedure is a knee replacement and further wherein the one or more real-time sensor data includes one or more of medial force, lateral force, position of the medial contact point and position of the lateral contact point.

4. The method of claim 3, wherein the one or more real-time sensor data further includes gap/displacement measurements and the effect of various resections on gap spacing.

5. The method of claim 1, wherein the next ligament balancing step comprises an ordered sequence of ligament balancing steps resulting in the target ligament balance state of the joint.

6. The method of claim 1, wherein the joint replacement procedure includes procedures selected from a group consisting of computer simulations of ligament balancing procedures, real-world surgeries performed by surgeons, surgeries performed or assisted by a robotic system and cadaver-based ligament balancing procedures.

7. The method of claim 1, wherein the assessment of the success of the ligament balancing is based on one or more of patient feedback, opinions of surgeons, force plates and foot mechanics of the patient and analysis of one or more of electromyography data, muscle-firing patterns, joint stability.

8. The method of claim 1, wherein the machine learning algorithm is further trained on surgical preferences of one or more surgeons.

9. The method of claim 1, wherein the machine learning algorithm is trained for each ligament individually.

10. The method of claim 1, wherein the machine learning algorithm is a neural network trained to recognize features in the real-time sensor data and the surgical parameters and to predict the ligament balancing steps based on the recognized features.

11. A system for intra-operative ligament balancing of a joint of a patient comprising:

at least one processor;

one or more sensors coupled to the processor;

a machine learning model; and software, stored on one or more non-transitory machine-readable storage media that, when executed by the one or more processors, cause the system to:

receive, by the at least one processor, one or more surgical parameters associated with the ligament balancing of the joint and input the one or more surgical parameters to the machine learning model;

receive, by the at least one processor, from the one or more sensors, real-time sensor data indicative of at least one or more characteristics of the joint and input the real-time sensor data to the machine learning model;

compute, by the at least one processor, using the machine learning model, a pattern indicated by the one or more surgical parameters and the real-time sensor data, wherein the machine learning model is trained on a plurality of input data values from previous joint replacement procedures;

compute, by the machine learning model, a next ligament balancing step based on the pattern, wherein data corresponding to the next ligament balancing step is outputted by the processor;

iteratively repeat, by the machine learning algorithm, computation of a subsequent ligament balancing step based on the real-time sensor data and the one or more surgical parameters inputted into the at least one processor, wherein one or more ligament balancing results, for each computation, are outputted by the at least one processor;

assess, by the at least one processor, a success of the ligament balancing, for each of the one or more ligament balancing results, relative to a target ligament balance state identified by the machine learning model; and perform, by the at least one processor, an iteration of training the machine learning model using one or more real-time sensor data and one or more surgical parameters associated with the target ligament balancing state.

12. The system of claim 11, wherein:

the one or more sensors comprise a load sensor; and the real-time sensor data is indicative of a force applied to the load sensor by a bone of the joint.

13. The system of claim 12, wherein: the joint is a knee and the bone is a femur; and the real-time sensor data is indicative of a plurality of forces applied to the load sensor by the femur at a plurality of points between flexion and extension of the knee.

14. The system of claim 13, wherein the real-time sensor data includes one or more of medial force, lateral force, position of the medial contact point and position of the lateral contact point.

15. The system of claim 14, wherein the real-time sensor data further includes gap/displacement measurements and the effect of various resections on gap spacing.

16. The system of claim 11, wherein:

the one or more sensors comprise an optical sensor; and the real-time sensor data is indicative of a displacement between bones of the joint.

17. The system of claim 11, wherein a ligament balancing step includes ligament releases and bony cuts.

18. The system of claim 11, further comprising:

one or more a robotic components controlled by the software and configured to perform the next ligament balancing step.

19. The system of claim 11, wherein the one or more surgical parameters comprise one or more of demographic data of the patient, muscularity of the patient, ligament condition of the patient, deterioration levels of various joint structures of the patient, collagen levels of the patient, ligament elasticity of the patient, prior injuries of the patient and patient activities.

20. The system of claim 11, wherein the machine learning model is a neural network trained to recognize features in the real-time sensor data and the one or more surgical parameters and to predict the subsequent ligament balancing step based on the recognized features.

* * * * *